United States Patent [19]

McKelvey

[11] 4,083,115
[45] Apr. 11, 1978

[54] DENTAL SALIVA EJECTOR

[76] Inventor: Thomas H. McKelvey, 645 First St., Suite E, Macon, Ga. 31201

[21] Appl. No.: 666,588

[22] Filed: Mar. 15, 1976

[51] Int. Cl.² .............................................. A61C 17/04
[52] U.S. Cl. ...................................................... 32/33
[58] Field of Search ............... 285/DIG. 22; 128/276; 232/33; 32/22, 26, 27

[56] References Cited

U.S. PATENT DOCUMENTS

| 2,574,135 | 11/1951 | Ward | 32/33 |
| 3,640,552 | 2/1972 | Demer | 385/DIG. 202 |
| 3,863,635 | 2/1975 | Swatman | 32/33 |

Primary Examiner—Robert Peshock
Attorney, Agent, or Firm—Roylance, Abrams, Berdo & Kaul

[57] ABSTRACT

A dental saliva ejector in which the ejector tube is equipped with a free-swivelling connector for connection to a suction conduit, the outlet end portion of the ejector tube being removably engaged in the bore of one member of the swivel connector in a resiliently compressed force fit, the swivel connector comprising two members which can be separated for cleaning.

5 Claims, 5 Drawing Figures

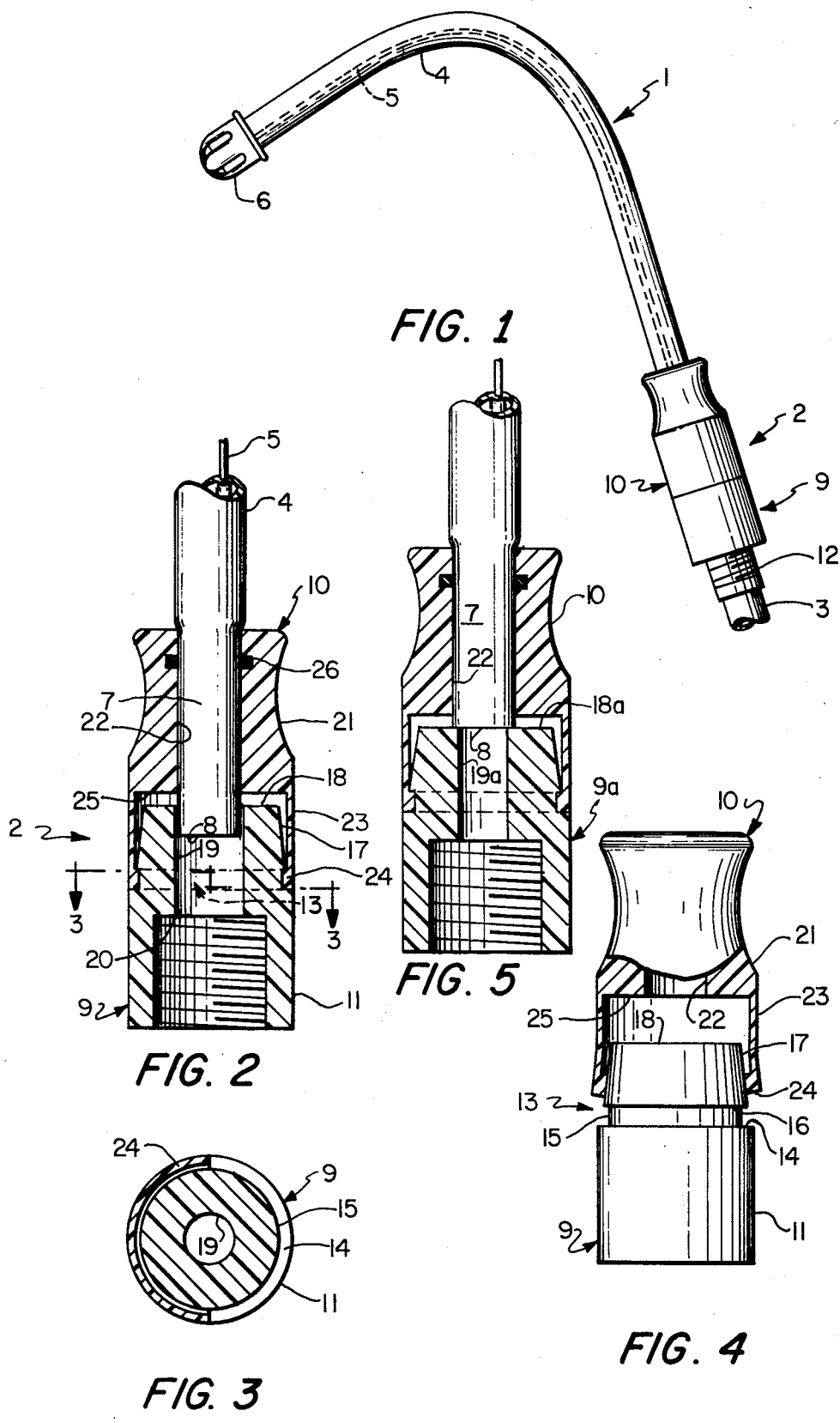

DENTAL SALIVA EJECTOR

BACKGROUND OF THE INVENTION

It is conventional dental practice to employ an evacuating device, commonly called a saliva ejector, for removing saliva and debris from the mouth of the patient during the performance of such dental work as cleaning and filling teeth. The usual dental saliva ejector comprises an ejector tube having the general form of a J, the tip of the shorter arm of the J constituting an inlet end to receive the saliva and any debris entrained therein, the tip of the stem of the J being connected to a hose which communicates with a source of reduced pressure. In many saliva ejectors, connection of the ejector tube to the hose is accomplished by a one-piece tubular connector, the outlet end of the ejector tube being forced into one end of the connector, the other end of the connector being internally threaded for attachment to an externally threaded connector member on the end of the hose. In such ejectors, the ejector tube can be rotated, relative to the connector and the hose, by holding the connector with one hand and using the other hand to apply enough force to the ejector tube to overcome the frictional engagement of the ejector tube in the connector. In other saliva ejectors, the ejector tube is connected to the hose by a swivel joint, so that rotation of the ejector tube is more easily accomplished. The general state of the art is illustrated by the following U.S. Pat. Nos. 2,130,406 —Angell; 2,519,595—Older; 3,460,253—Hutson; 3,541,583—Deuschle; 3,645,497—Nyboer; 3,758,950—Krouzian; 3,864,831—Drake; 3,890,712—Lopez. While prior-art saliva ejectors have been widely adopted, there has been a continuing need for improvements which would allow such free swivelling of the ejector tube that ajustment of the tube in the patient's mouth could be accomplished by manipulating the tube between the thumb and forefinger of one hand, yet would not involve an unduly expensive swivel connector and which would allow complete and easy disassembly for cleaning.

OBJECTS OF THE INVENTION

A general object of the invention is to devise a swivelled saliva ejector which is of inexpensive construction yet allows the ejector tube to be adjusted with the thumb and forefinger of one hand.

Another object is to provide such a device which can be completely disassembled, cleaned and reassembled without exercise of mechanical skill or the use of tools.

A further object is to provide such a device wherein all parts of the connector can be fabricated from a rigid polymeric material of such nature that all surfaces will be easily cleanable and will have a minimum tendancy to accept and retain foreign materials.

Yet another object is to devise a saliva ejector which is leak-free, yet swivels freely and does not require complex or expensive sealing features.

A still further object is to provide such a device in which debris entrained in the saliva does not enter the working area of the swivel connector.

SUMMARY OF THE INVENTION

Saliva ejectors according to the invention comprise an ejector tube and a swivel connector. The outlet end portion of the tube is of a resiliently deformable polymeric material and is forced through an axial bore in the body of a female connector member. The connector includes a male connector member having a first portion adapted to be connected to the evacuating hose, as by screw threads, the male member also having a shank provided with an outer transverse annular groove and an outer surface portion which tapers inwardly from the groove toward the tip of the shank. The female connector member has an axially projecting thin-walled sleeve equipped with an inwardly projecting transverse annular flange dimensioned to engage with a snap fit in the groove presented by the shank of the male connector member. The shank of the male connector member has a through bore which advantageously is of larger transverse dimension than and receives the end of the ejector tube. With the device fully assembled, and the hose connected to a source of reduced pressure, fluid flow adequate for evacuation via the ejector tube and the bore of the male connector member is established, and a small air flow is induced via the space between the connector members to prevent leakage.

In order that the manner in which the foregoing and other objects are achieved according to the invention can be understood in detail, particularly advantageous embodiments thereof will be described with reference to the accompanying drawings, which form a part of the original disclosure hereof, and wherein:

FIG. 1 is a side elevational view of a saliva ejector in accordance with one embodiment of the invention;

FIG. 2 is a longitudinal sectional view of a swivel connector forming part of the device of FIG. 1;

FIG. 3 is a transverse sectional view taken generally on line 3—3, FIG. 2;

FIG. 4 is a side elevational view of the connector of FIGS. 2 and 3 with a portion of the female connector member broken away for clarity of illustration, showing the manner in which the connector is assembled and disassembled, and FIG. 5 is a view similar to FIG. 2 of a swivel connector according to another embodiment of the invention.

DETAILED DESCRIPTION OF THE EMBODIMENT OF FIGS. 1-4

In this embodiment, the saliva ejector comprises an ejector tube 1 and a swivel connector 2 via which the ejector tube is connected to a hose 3, FIG. 1, which according to usual practice extends to a dental unit (not shown) and communicates with a source of reduced pressure. Ejector tube 1 can be of conventional type, comprising a length of resiliently deformable tubing 4 having a metal wire 5 incorporated therein as a stiffener, the tube being bent into the general form of a J and retaining that shape because of the stiffening wire. The tip of the shorter arm of the J is equipped with a slotted inlet cap 6 and constitutes the inlet for saliva and entrained debris. The longer arm of the J terminates in outlet end portion 7, FIG. 2, which has a flat annular end surface 8 lying in a plane at right angles to the longitudinal axis of portion 7.

Connector 2 comprises a male connector member 9 and a female connector member 10 both formed, as by injection molding, from a rigid polymeric material having low moisture absorption, high impact strength, stiffness and yield stress. Advantageously, members 9 and 10 are of an acetal resin, i.e., a polyoxymethylene polymer, such as the resin marketed by E. I. duPont de Nemours & Co., Inc., Wilmington, Delaware 19898, under the trademark DELRIN. Such resins are available in non-yellowing white formulations and, when molded, present slick surfaces which are easily cleaned and have little tendancy to accept and retain foreign materials.

Member 9 includes a first tubular portion 11 having a right cylindrical outer surface of larger diameter, portion 11 being internally threaded for connection to a threaded fitting 12, FIG. 1, on hose 3. Member 9 also includes a shank which is integral with and projects axially from portion 11 and is provided with an outwardly opening transverse annular groove 13, FIG. 4, defined by a first shoulder 14 at the end of portion 11, a right cylindrical bottom surface 15, and a second shoulder 16, the outer diameter of shoulder 16 being smaller than that of shoulder 14. The main outer surface 17 of the shank is frustoconical, tapering inwardly from shoulder 16 toward the tip of the shank. At its tip, the shank has a flat transverse end face 18. An axial through bore 19 extends through the shank and is of a diameter slightly larger than that of outlet end 8 of the ejector tube. The inner diameter of the threaded portion of member 9 is large compared to bore 19 so that there is a transverse annular shoulder 20, FIG. 2, against which a suitable screen or filter element can be held by fitting 12.

Female connector member 10 includes a body portion 21 having an axial through bore 22 of a diameter slightly smaller than the outer diameter of tubing 4 when the tubing is in relaxed undeformed condition. Projecting from one end of body portion 21 is a thin-walled sleeve 23 which terminates at its free end in a transverse annular inwardly directed flange 24 dimensioned to engage in and substantially fill groove 13 of member 9. Body portion 21, sleeve 23 and flange 24 are integral. The outer diameter of sleeve 23 is equal to the outer diameter of body portion 21 at the juncture of the sleeve and body portion. The inner diameter of sleeve 23 is large as compared to the diameter of bore 22, and there is a flat transverse annular shoulder 25, FIG. 2, at the end of body portion 21 to which sleeve 23 is joined. Near the opposite end of body portion 21, bore 22 is interrupted by a transverse annular groove which accomodates an O-ring 26 of elastomeric material. The outer surfaces of sleeve 23 and the part of body portion 21 adjacent the sleeve are right cylindrical when the sleeve is relaxed and undeformed. Over most of its length, however, the outer surface of body portion 21 is annularly concave, as seen in FIG. 4, to provide for positive engagement of the body portion between the thumb and forefinger.

For assembly of the device, the outlet end portion 7 of ejector tube 1 is pushed into and through bore 22 of connector member 10 until the tip of portion 7 projects beyond shoulder 25, FIG. 2. As a result, portion 7 is deformed radially inwardly, engaging the wall of bore 7 in a compressive force fit and being engaged by O-ring 26 in good fluid-tight sealing relation. To assemble the swivel connector 2, female connector member 10 is forced toward member 9, with flange 24 embracing the tapered surface 17 of the shank, in the manner seen in FIG. 4, this operation being continued until flange 24 reaches and snaps into groove 13.

Though rigid in the sense of meeting the required minimum elasticity when tested in accordance with ASTM D747, D790, D639 or D882 (ASTM D883-65T), the polymeric materials suitable for female connector member 10 have substantial resilience, allowing outward deformation of sleeve 23 in the manner shown in FIG. 4, followed by return of the sleeve to its original relaxed configuration when flange 23 reaches groove 13. The return to relaxed configuration is immediate and essentially complete, so that flange 24 is positively retained in groove 13 and there is low-friction rubbing engagement between the circular surfaces of the flange and groove. Thus, while members 9 and 10 are locked securely together against significant axial relative movement, the interengaged flange and groove act as a low-friction bearing with respect to rotation of member 10, about the axis of the connector, relative to member 9, and adjustment of the position of tip 6 of the ejector in the patient's mouth can be accomplished easily by use of only the thumb and forefinger of one hand.

From FIG. 2, it will be seen that, in the assembled device, shoulder 25 is spaced a significant distance from end face 18 of the shank of the male connector member, and that there is a significant annular space between frusto-conical surface 17 and the inner surface of sleeve 23. As a final step of assembly, outlet portion 7 of the ejector tube is pushed further through member 10 to insert end 8 thereof into through bore 19 of male member 9. While flange 24 substantially fills groove 13, the mating surfaces of the flange and groove are in only rubbing engagement. With hose 3, FIG. 1, connected to the usual reduced pressure source, the interior space defined by surfaces 17, 18, 25 and the inner surface of sleeve 23 is evacuated and a very small air flow is established from outside of the connector via groove 13. The end 8 of the ejector tube is disposed within the adjacent end of bore 19 so that a significant portion of the tube is surrounded by the wall of the bore, and there is only a small space between tube end 8 and the surrounding wall of bore 19. Accordingly, while there is substantial flow of saliva and entrained debris via ejector tube 1 and bore 19 in series, there is little or no opportunity for saliva and debris to escape from the outlet end portion 7 of the ejector tube into the space between surfaces 18 and 25.

Ejector tube 1 is fabricated conventionally, and the material of tubing 4 can be any of the flexible, resiliently deformable polymeric materials. Advantageously, tubing 4 is of a highly plasticized polyvinyl chloride formulation chosen for both flexibility and resilient deformability. Tubing extruded from such materials has adequate strength to maintain its tubular form, yet is sufficiently deformable to allow the radial compression necessary to allow outlet portion 7 to be pushed through bore 22. In the assembled device, compression of outlet portion 7 causes the outer surface of that portion to be firmly and uniformly engaged with the wall of bore 22, tending to establish a good seal between member 10 and the ejector tube. That seal is further aided by inclusion of the O-ring 26. Accordingly, essentially all of the pressure differential applied via the engaged surfaces 8 and 18 is effective to evacuate the space defined by surfaces 17, 18, 25 and the inner surface of sleeve 23.

EMBODIMENT OF FIG. 5

FIG. 5 illustrates a second embodiment of the invention wherein female connector member 10 is an hereinbefore described, but male member 9a is modified so that the diameter of bore 19a is slightly smaller than the outer diameter of end 8 of the ejector tube. In this embodiment, outlet end portion 7 of the ejector tube is forced through bore 22 until end 8 is in flush rubbing engagement with the flat end face 18a of the male member. Through bore 19a thus serves as an extension of the bore of the outlet end portion 7 of the ejector tube, and the suction effect provided by hose 3 evacuates the interior of the swivel connector because of air flow between end face 18a and the end face of tube end 8. Again, there is little or no opportunity for debris to escape into the interior of the swivel.

While particularly advantageous embodiments have been chosen to illustrate the invention, it will be apparent that various changes and modifications can be made without departing from the scope of the invention as defined in the appended claims. Thus, for example, the tip of the shank can be formed with a socket to receive the tip of outlet portion 7 of the ejector tube.

What is claimed is:

1. In a dental saliva ejector, the combination of
an ejector tube having an inlet end to be placed in the patient's mouth and an outlet end portion spaced from said inlet end,
at least said outlet end portion being of a resiliently deformable polymeric material;
a male tubular connector member comprising
a first portion of larger outer transverse dimension adapted to be connected to a conduit to communicate with a source of reduced pressure, and
a shank projecting axially from said first portion;
said shank being provided with an outwardly opening transverse annular first groove at the end of said shank adjacent said first portion, an outer surface portion which tapers inwardly from said first groove toward the tip of the shank, a transverse end face and an axial through bore which opens through said end face;
a tubular female connector member comprising
a body portion having an axial through bore with a transverse dimension slightly smaller than the outer diameter of said outlet end portion of the ejector tube, said throughbore being interrupted by a transverse annular second groove, and
a sleeve portion extending from one end of said body portion and terminating in a transverse annular inwardly directed flange dimensioned to engage in said first groove,
said first groove and said flange being circular, whereby said male and female connector members can be rotated relative to each other;
said outlet end portion of the ejector tube extending through the axial through bore of said body portion in force-fit relation such that the material of said outlet end portion is inwardly compressed by the wall of the axial through bore; and
a sealing ring disposed in said second groove and providing a fluid-tight seal between said body portion of said female connector and said ejector tube.

2. The combination according to claim 1, wherein said second groove is located adjacent the end of said body portion which is opposite said skirt.

3. In a dental saliva ejector, the combination of
an ejector tube having an inlet end to be placed in the patient's mouth and an outlet end portion spaced from said inlet end,
at least said outlet end portion being of a resiliently deformable polymeric material;
a male tubular connector member comprising
a first portion of larger outer transverse dimension adapted to be connected to a conduit to communicate with a source of reduced pressure, and
a shank projecting axially from said first portion;
said shank being provided with an outwardly opening transverse annular groove at the end of said shank adjacent said first portion, an outer frusto-conical surface portion which tapers inwardly from said groove toward the tip of the shank, a transverse end face, and an axial through bore which opens through said end face;
a tubular female connector member operatively engaged with said male connector member and comprising
a body portion having an axial through bore with a transverse dimension slightly smaller than the outer diameter of said outlet end portion of the ejector tube,
a thin-walled cylindrical sleeve portion extending from one end of said body portion and terminating in a transverse annular inwardly directed flange engaged in said groove of said shank of the male connector member, and
a transverse annular shoulder at the juncture between said body portion and said sleeve portion,
there being a significant internal space defined by the combination of said frusto-conical surface of said shank, the inner surface of said sleeve portion, said end face of said shank, and said shoulder,
said flange contacting the bottom of said groove with a rubbing engagement and said groove and flange being circular, whereby said male and female connector members can be rotated relative to each other in non-sealing engagement;
said outlet end portion of the ejector tube extending within the axial through bore of said shank in force-fit relation such that the material of said outlet end portion is inwardly compressed by the wall of the axial through bore; and
means establishing an effective fluid-tight seal between said body portion of said female connector member and said outlet end portion of the ejector tube;
said body portion of said female connector member carrying, at the end thereof which joins said sleeve portion, a tubular projection extending from said shoulder into said axial through bore of said shank of said male connector member,
said projection communicating with the interior of the ejector tube and being spaced inwardly from the wall of said axial through bore of said shank, whereby said axial through bore of said shank communicates with said significant internal space via the space between said projection and the wall of said axial through bore of said shank, connection of said male connector to a source of reduced pressure causing a small flow of air into said significant internal space via said groove and from said significant internal space into the axial through bore of said shank via the space between said projection and the wall of said axial through bore of said shank, whereby during use of the saliva ejector, saliva and debris are prevented from reaching the area of rubbing engagement between said flange and the bottom of the groove.

4. The combination according to claim 3, wherein said outlet end portion of the ejector tube extends completely through said body portion of said female connector member and said tubular projection is the tip of said outlet end portion of the ejector tube.

5. In a dental saliva ejector, the combination of an ejector tube having an inlet end to be placed in the patient's mouth and an outlet end portion spaced from said inlet end,
at least said outlet end portion being of a resiliently deformable polymeric material; a male tubular connector member comprising
a first portion adapted to be connected to a conduit to communicate with a source of reduced pressure,
a shank projecting axially from said first portion,
said shank having an outwardly opening transverse annular groove at the end of the shank adjacent said first portion, an outer frusto-conical surface portion tapering from said groove toward the tip of the shank, and an axial through bore;
a tubular female connector member comprising
a body portion having an axial through bore with a transverse dimension slightly smaller than the outer diameter of said outlet end portion of the ejector tube, and
a thin-walled cylindrical sleeve portion extending from one end of said body portion concentric with the through bore of said body portion and terminating in a transverse annular inwardly directed flange having an inner diameter significantly smaller than the largest outer diameter of said frusto-conical surface portion;
said flange being engaged in said groove, the inner surface of said sleeve portion surrounding but being spaced outwardly from said frusto-conical surface portion, and the tip of said shank being spaced axially from said body portion of said female connector member, whereby the internal space between said sleeve portion and said shank adjacent said groove is in communication with the through bore of said shank and thus with the source of reduced pressure when the saliva ejector is in use;
said outlet end portion of said ejector tube extending within the axial through bore of the body portion of said female connector unit in force-fit relation such that the material of said outlet end portion is inwardly compressed by the wall of the through bore; and
means establishing an effective fluid-tight seal between the body portion of said female connector member and the outlet end portion of said ejector tube;
said body portion and said sleeve portion of said female connector member constituting portions of an integral piece of polymeric material, the resilience of the polymeric material and the relative dimensions of said flange and said groove being such as to establish a low-friction rubbing engagement of said flange in said groove, the capability of relative rotation between the male and female connector member,
connection of the through bore of said male connector member to a source of reduced pressure being effective to cause air to flow into the internal space between said sleeve portion and said shank via said groove and thence into the through bore of said male connector member, whereby during use of the saliva ejector saliva and debris are prevented from reaching said groove.

* * * * *

UNITED STATES PATENT OFFICE
CERTIFICATE OF CORRECTION

PATENT NO. : 4,083,115
DATED : April 11, 1978
INVENTOR(S) : Thomas H. McKelvey

It is certified that error appears in the above-identified patent and that said Letters Patent are hereby corrected as shown below:

Column 8, line 21, after "groove," insert --thereby affording--.

Signed and Sealed this

Tenth Day of October 1978

[SEAL]

Attest:

RUTH C. MASON
Attesting Officer

DONALD W. BANNER
Commissioner of Patents and Trademarks